United States Patent

Anderson et al.

[11] 3,945,998
[45] Mar. 23, 1976

[54] HERBICIDAL 4-BENZYLOXYMETHYL OXAZOLINES

[75] Inventors: Martin Anderson, Whitstable; Peter H. Kirkham, Sittingbourne, both of England

[73] Assignee: Shell Oil Company, Houston, Tex.

[22] Filed: July 3, 1972

[21] Appl. No.: 268,295

[30] Foreign Application Priority Data
July 1, 1971 United Kingdom............... 30868/71

[52] U.S. Cl.................... 260/240 D; 71/88; 71/94; 260/295 R; 260/307 F
[51] Int. Cl.².................................. C07D 263/14
[58] Field of Search ......... 260/307 F, 296 R, 240 D

[56] References Cited
UNITED STATES PATENTS
3,414,620  12/1968  Bresson et al. .................... 260/584

Primary Examiner—Raymond V. Rush

[57] ABSTRACT

Oxazoline derivatives of the formula

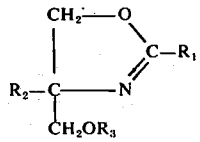

wherein $R_1$ is optionally substituted alkyl, alkenyl, aryl, aralkyl, aralkenyl, alkaryl, or heterocyclic, $R_2$ is alkyl and $R_3$ is optionally substituted aralkyl, are useful as herbicides.

6 Claims, No Drawings

HERBICIDAL 4-BENZYLOXYMETHYL OXAZOLINES

BACKGROUND OF THE INVENTION

1. Field of the Invention

This invention relates to a novel class of oxazoline derivatives, to herbicidal compositions containing them, and to their use as herbicides.

2. Description of the Prior Art

A search of the prior art has not discovered any of the herbicidal oxazolines of this invention.

SUMMARY OF THE INVENTION

It has now been found that certain novel oxazoline derivatives exhibit herbicidal activity enabling control of certain economically important weed species.

DESCRIPTION OF THE PREFERRED EMBODIMENTS

The present invention relates to oxazoline derivatives of the formula

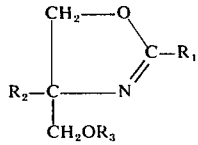

wherein $R_1$ is optionally substituted alkyl, alkenyl, aryl, aralkyl, aralkenyl, alkaryl, or heterocyclic, $R_2$ is alkyl and $R_3$ is optionally substituted aralkyl. Examples of suitable substituents in the optionally substituted groups include halogen, nitro, alkoxy or phenoxy.

Preferred derivatives of the above formula are those wherein $R_1$ is alkyl of from 1 to 12 carbon atoms, or trifluoromethyl; alkenyl of up to 6 carbon atoms; phenalkyl of up to 12 carbon atoms; phenyl; phenyl substituted by one or more of halogen, nitro, alkyl or alkoxy of from 1 to 6 carbon atoms; benzyl; benzyloxy; 5- or 6-membered heterocyclic containing one nitrogen or oxygen atom; $R_2$ is alkyl of 1-6 carbon atoms; $R_3$ is benzyl, or benzyl substituted by one or more of halogen, nitro, alkyl of 1-6 carbon atoms, phenyl or phenoxy.

The oxazoline derivatives of this invention may be prepared by a process which comprises reacting a hydroxymethyl compound of the formula:

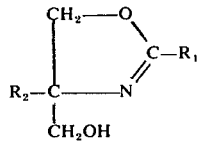

with a strong base and a halide of formula:

wherein Hal represents a halogen, suitable chlorine, atom and each of the symbols has the meaning already ascribed to it. The strong base is suitably an alkali metal hydride, for example sodium hydride and the reaction is conveniently carried out in an aromatic hydrocarbon, for example toluene, as solvent.

In certain cases the oxazoline derivatives are more conveniently prepared by an alternative process which comprises reacting a substituted aminopropanol of the formula:

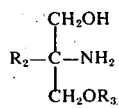

with a carboxylic acid of the formula:

The reaction is also conveniently carried out in an aromatic hydrocarbon, for example xylene, as solvent.

The oxazoline derivatives of the invention are of interest as herbicides. The invention includes therefore herbicidal compositions comprising a carrier and/or a surface-active agent together with, as active ingredient, at least one oxazoline derivative of the invention. Likewise the invention includes also a method of combatting undesired plant growth at a locus which comprises applying to the locus a herbicidally effective amount of an oxazoline derivative or composition of the invention.

The term "carrier" as used herein means solid or fluid material, which may be inorganic or organic and of synthetic or natural origin, with which the active compound is mixed or formulated to facilitate its application to the plant, seed, soil or other object to be treated, or its storage, transport or handling.

Suitable solid carriers are natural and synthetic clays and silicates for example natural silicas such as diatomaceous earths; magnesium silicates, for example, talcs; magnesium aluminum silicates, for example, attapulgites and vermiculites; aluminum silicates, for example kaolinites, montmorillonites and micas; calcium carbonates; calcium sulfate; synthetic hydrated silicon oxides and synthetic calcium or aluminum silicates; elements such as for example, carbon and sulfur; natural and synthetic resins such as, for example, coumarone resins, polyvinyl chloride and styrene polymers and copolymers; solid polychlorophenols; bitumen, waxes such as for example, beeswax, paraffin wax, and chlorinated mineral waxes; and solid fertilizers, for example superphosphates.

Examples of suitable fluid carriers are water, alcohols, such as for example, isopropanol, glycols; ketones such as for example, acetone, methyl ethyl ketone, methyl isobutyl ketone and cyclohexanone; ethers; aromatic hydrocarbons such as for example, benzene, toluene and xylene; petroleum fractions such as for example, kerosene, light mineral oils; chlorinated hyrocarbons, such as for example, carbon tetrachloride, perchloroethylene, trichloroethane, including liquified normally vaporous gaseous compounds. Mixtures of different liquids are often suitable.

The surface active agent may be an emulsifying agent or a dispersing agent or a wetting agent; it may be nonionic or ionic. Any of the surface-active agents usually applied in formulating herbicides or insecticides may be used. Examples of suitable surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols for example p-octylphenol or p-octylcresol, with ethylene oxide and/or propylene oxide; sulfates or sulfonates of these condensation products, alkali or alkaline earth metal salts, preferably sodium salts, of sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates and aerosols. Wettable powders are usually compounded to contain 25, 50 or 75% by weight of toxicant and usually contain in addition to solid carrier, 3–10% by weight of a dispersing agent and, where necessary, 0–10% by weight of stabilizer(s) and/or other additives such as penetrants or stickers. Dusts are usually formulated as a dust concentrate having a similar composition to that of a wettable powder but without a dispersant, and are diluted in the field with further solid carrier to give a composition usually containing ½–10% by weight of toxicant. Granules are usually prepared to have a size between 10 and 100 BS mesh (1.676–0.152 mm), and may be manufactured by agglomeration or impregnation techniques. Generally granules will contain ½–25% by weight toxicant and 0–10% by weight of additives such as stabilizers, slow release modifiers and binding agents. Emulsifiable concentrates usually contain, in addition to the solvent and, when necessary, co-solvent, 10–50% weight per volume toxicant, 2–20% weight per volume emulsifiers and 0–20% weight per volume of appropriate additives such as stabilizers, penetrants and corrosion inhibitors. Suspension concentrates are compounded so as to obtain a stable, non-sedimenting, flowable product and usually contain 10–75% w toxicant, 0.5–15% w of dispersing agents, 0.1–10% w of suspending agents such as protective colloids and thixotropic agents, 0–10% w of appropriate additives such as defoamers, corrosion inhibitors, stabilisers, penetrants and stickers, and as carrier, water or an organic liquid in which the toxicant is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick 'mayonnaise'-like consistency.

The composition of the invention may also contain other ingredients, for example, other compounds possessing pesticidal, especially insecticidal, acaricidal, herbicidal or fungicidal, properties.

The invention is further illustrated in the following examples. In each of these examples, the identify of the product was confirmed by analyses.

EXAMPLE 1

4-Benzyloxymethyl-4-methyl-2-phenyloxazoline (Compound 1)

A suspension of 4-hydroxymethyl-4-methyl-2-phenyloxazoline (19.1 grams, prepared by the method described in J. Amer, Chem. Soc. 1945, 67, 1069) in toluene (200 milliliters) was added slowly to a stirred suspension of sodium hydride (2.4 grams) in toluene (50 milliliters). Some warming was necessary to initiate the reaction. The mixture was then heated under reflux for 2 hours with stirring. Benzyl chloride (13.0 grams) was added to the mixture over a period of 10 minutes. The mixture was heated under reflux for a further 5 hours and then allowed to stand at room temperature for 16 hours. The mixture was washed with water (3 × 200 milliliters), dried ($MgSO_4$) and evaporated under reduced pressure. The residue was distilled in vacuo to give the desired product, boiling point 147°–149°C at 0.3 Torr.

EXAMPLE II

4-Benzyloxymethyl-4-methyl-2-(4-nitrophenyl)oxazoline (Compound 2)

a. Preparation of 2-amino-3-benzyloxy-2-methylpropanol 2,4-Dimethyl-4-benzyloxymethyloxazoline (80 grams, prepared by a similar method to that described in Example 1) and potassium hydroxide (100 grams) in aqueous ethanol were heated together under reflux for 4 days. The volume of the reaction mixture was reduced under reduced pressure and water (300 milliliters) was then added. The aqueous mixture was extracted with ether (3 × 250 milliliters) and the extracts dried and the solvent removed under reduced pressure. The residue was distilled under reduced pressure to give 2-amino-3-benzyloxy-2-methylpropanol as a colorless liquid, boiling point 128°–129°C at 1.1 Torr.

b. Preparation of 4-benzyloxymethyl-4-methyl-2-(4-nitrophenyl)oxazoline

2-Amino-3-benzyloxy-2-methylpropanol (13.5 grams) and 4-nitrobenzoic acid (11.7 grams) in dry xylene (100 milliliters) were heated together under reflux for 24 hours using a Dean-Stark trap for collection of the water formed during the reaction. The cooled solution was evaporated to dryness under reduced pressure and the residue was treated with ether and allowed to stand for 15 hours at 0°C. The yellow solid formed was recrystallized from ethanol to yield the desired product, melting point 65°–66°C.

EXAMPLE 3

Following procedures similar to those of examples 1 and 2 the following further compounds were prepared, covering the indicated physical characteristics.

Compound $$R_2-\underset{CH_2OR_3}{\overset{CH_2-O}{C}}\diagdown \overset{}{\underset{N}{C}}-R_1$$

| No. | $R_1$ | $R_2$ | $R_3$ | Melting point °C, or boiling point, °C/Torr. |
|---|---|---|---|---|
| 3 | benzyl | methyl | benzyl | 165 – 168/0.6 |
| 4 | methyl | methyl | benzyl | 119 – 120/2.3 |
| 5 | 4-meth- | methyl | benzyl | 186 – 186/188/0.35 |

-continued

Compound

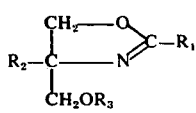

| No. | R₁ | R₂ | R₃ | Melting point °C, or boiling point, °C/Torr. |
|---|---|---|---|---|
| | oxyphenyl | | | |
| 6 | 4-chlorophenyl | methyl | benzyl | 40 – 41 |
| 7 | 3-pyridyl | methyl | benzyl | 174 – 175/0.75 |
| 8 | phenyl | methyl | 2-chlorobenzyl | 166 – 192/0.4 |
| 9 | phenyl | methyl | 4-chlorobenzyl | 55 – 57 |
| 10 | phenyl | methyl | 2,6-dichlorobenzyl | 82 – 84 |
| 11 | phenyl | methyl | 4-methylbenzyl | 190 – 194/1.0 |
| 12 | 4-fluorophenyl | methyl | benzyl | oil |
| 13 | 2-furyl | methyl | benzyl | oil |
| 14 | decyl | methyl | benzyl | 180 – 186/0.25 |
| 15 | 4-pyridyl | methyl | benzyl | 174 – 178/0.75 |
| 16 | p-tolyl | methyl | benzyl | 177 – 184/0.8 |
| 17 | styryl | methyl | benzyl | 203 – 204/0.9 |
| 18 | 2-propenyl | methyl | benzyl | 113 – 119/1.0 |
| 19 | o-tolyl | methyl | benzyl | 188 – 193/3.0 |
| 20 | trifluoromethyl | methyl | benzyl | 119 – 132/0.3 |
| 21 | phenyl | methyl | 3-methylbenzyl | 177 – 188/2.3 |
| 22 | phenyl | methyl | 4-nitrobenzyl | 92 – 94 |
| 23 | methyl | ethyl | benzyl | 152 – 158/1.0 |
| 24 | phenyl | ethyl | benzyl | 176 – 179/0.8 |
| 25 | 2-chlorobenzyl | methyl | benzyl | 202 – 204/2.0 |
| 26 | o-tolyl | ethyl | benzyl | 196 – 198/2.5 |
| 27 | 2-furyl | ethyl | benzyl | oil |
| 28 | 2-methoxyphenyl | methyl | benzyl | oil |

EXAMPLE 4

Herbicidal Activity

To evaluate their herbicidal activity, the compounds of the invention were tested using as a representative range of plants: maize, *Zea mays* (Mz); rice, *Oryza sativa* (R); barnyard grass, *Echinchloa crus-galli* (BG); pea, *Pisum sativum* (P); linseed, *Linum usitatissium* (L); mustard, *Sinapis alba* (M); and sugar beet, *Beta vulgaris* (SB).

The tests fall into two categories, pre-emergence and post-emergence. The pre-emergence tests involved spraying a liquid formulation of the compound onto the soil in which the seeds of the plant species mentioned above had recently been sown. The post-emergence tests involved two types of test, viz. soil drench and foliar spray tests. In the soil drench tests the soil in which seedling plants of the above species were growing, was drenched with a liquid formulation containing a compound of the invention, and in the foliar spray tests the seedling plants were sprayed with such a formulation.

The soil used in the tests was a steam-sterilised, modified John Innes Compost mixture in which half the peat, by loose bulk, had been replaced by vermiculite.

The formulations used in the tests were prepared by diluting with water solutions of the compounds in acetone containing 0.4% by weight of an alkylphenol/ethylene oxide condensate available under the trade mark Triton X-155. In the soil spray and foliar spray tests the acetone solutions were diluted with an equal volume of water and the resulting formulations applied at two dosage levels corresponding to 10 and 1 kilograms of active material per hectare respectively in a volume equivalent to 400 liters per hectare. In the soil drench tests one volume of the acetone solution was diluted to 155 volumes with water and the resulting formulation applied at one dosage level equivalent to 10 kilograms of active material per hectare in a volume equivalent to approximately 3,000 liters per hectare.

In the pre-emergence tests untreated sown soil and in the post-emergence tests untreated soil bearing seedling plants were used as controls.

The herbicidal effects of the compounds were assessed visually seven days after spraying the foliage and drenching the soil and eleven days after spraying the soil, and were recorded on a 0–9 scale. A rating 0 indicates no effect on the treated plants, a rating 2 indicates a reduction in fresh weight of stem and leaf of the plants of approximately 25%, a rating 5 indicates a reduction of approximately 55%, a rating 9 indicates a reduction of 96% etc.

The results of the tests are set out in Table I.

TABLE I

| | | Post Emergence | | | | | | | | | | | | | | Pre-Emergence | | | | | | |
|---|---|---|---|---|---|---|---|---|---|---|---|---|---|---|---|---|---|---|---|---|---|---|
| | | Soil Drench | | | | | | | Foliar Spray | | | | | | | Soil Spray | | | | | | |
| Compound | Dosage Kilogram/hectare | Mz | R | BG | P | L | M | SB | Mz | R | BG | P | L | M | SB | Mz | R | BG | P | L | M | SB |
| 1 | 10 | 0 | 0 | 5 | 0 | 1 | 0 | 1 | 2 | 3 | 8 | 1 | 9 | 9 | 8 | 8 | 9 | 9 | 4 | 6 | 4 | 3 |
| | 1 | | | | | | | | 0 | 0 | 0 | 0 | 1 | 1 | 0 | 0 | 0 | 9 | 0 | 2 | 0 | 0 |
| 2 | 10 | 0 | 0 | 0 | 0 | 0 | 0 | 0 | 0 | 0 | 7 | 0 | 6 | 4 | 0 | 0 | 0 | 0 | 0 | 0 | 0 | 0 |
| | 1 | | | | | | | | — | — | 0 | — | 0 | 0 | — | — | — | — | — | — | — | — |
| 3 | 10 | 0 | 0 | 0 | 0 | 0 | 0 | 0 | 3 | 2 | 6 | 1 | 6 | 9 | 8 | 0 | 0 | 0 | 0 | 0 | 0 | 0 |
| | 1 | | | | | | | | 0 | 0 | 0 | 0 | 0 | 1 | 0 | — | — | — | — | — | — | — |
| 4 | 10 | 0 | 0 | 0 | 0 | 0 | 0 | 0 | 0 | 2 | 1 | 1 | 7 | 5 | 3 | 0 | 0 | 0 | 0 | 0 | 0 | 0 |
| | 1 | | | | | | | | — | 0 | 0 | 0 | 0 | 0 | 0 | — | — | — | — | — | — | — |
| 5 | 10 | 0 | 0 | 0 | 0 | 0 | 0 | 0 | 1 | 2 | 7 | 2 | 8 | 6 | 7 | 0 | 0 | 4 | 0 | 1 | 0 | 0 |
| | 1 | | | | | | | | 0 | 0 | 0 | 0 | 1 | 2 | 0 | — | — | 0 | — | 0 | — | — |
| 6 | 10 | 0 | 0 | 0 | 0 | 0 | 0 | 0 | 1 | 1 | 8 | 1 | 6 | 5 | 8 | 0 | 0 | 2 | 0 | 0 | 0 | 0 |
| | 1 | | | | | | | | 0 | 0 | 1 | 0 | 0 | 0 | 0 | — | — | 0 | — | — | — | — |
| 7 | 10 | 0 | 0 | 2 | 0 | 0 | 2 | 0 | 1 | 1 | 7 | 3 | 9 | 9 | 9 | 0 | 1 | 8 | 0 | 0 | 0 | 6 |
| | 1 | | | | | | | | 0 | 0 | 0 | 0 | 2 | 6 | 6 | — | 0 | 0 | — | — | — | 0 |
| 8 | 10 | — | — | — | — | — | — | — | 5 | 1 | 9 | 2 | 8 | 8 | 4 | 0 | 0 | 8 | 0 | 2 | 0 | 2 |
| | 1 | | | | | | | | 0 | 0 | 2 | 0 | 1 | 0 | 0 | — | — | 2 | — | 0 | — | 0 |
| 9 | 10 | 0 | 0 | 0 | 0 | 0 | 0 | 0 | 3 | 1 | 8 | 0 | 7 | 7 | 6 | 0 | 0 | 0 | 0 | 0 | 0 | 0 |
| | 1 | | | | | | | | 0 | 0 | 1 | — | 0 | 0 | 0 | — | — | — | — | — | — | — |
| 10 | 10 | 0 | 0 | 0 | 0 | 0 | 0 | 0 | 1 | 0 | 8 | 1 | 6 | 4 | 6 | 0 | 0 | 0 | 0 | 0 | 0 | 0 |
| | 1 | | | | | | | | 0 | — | 1 | 0 | 0 | 0 | 0 | — | — | — | — | — | — | — |
| 11 | 10 | 0 | 0 | 0 | 0 | 0 | 2 | 0 | 1 | 1 | 9 | 2 | 8 | 9 | 8 | 0 | 0 | 0 | 0 | 0 | 0 | 0 |
| | 1 | | | | | | | | 0 | 0 | 2 | 0 | 0 | 0 | 0 | — | — | — | — | — | — | — |
| 12 | 10 | 0 | 0 | 0 | 0 | 0 | 0 | 0 | 0 | 1 | 9 | 2 | 9 | 9 | 9 | 0 | 0 | 8 | 0 | 3 | 0 | 0 |

TABLE I-continued

| Compound | Dosage Kilogram/hectare | Post Emergence Soil Drench | | | | | | | Post Emergence Foliar Spray | | | | | | | Pre-Emergence Soil Spray | | | | | | |
|---|---|---|---|---|---|---|---|---|---|---|---|---|---|---|---|---|---|---|---|---|---|---|
| | | Mz | R | BG | P | L | M | SB | Mz | R | BG | P | L | M | SB | Mz | R | BG | P | L | M | SB |
| 13 | 10 | 6 | 5 | 7 | 2 | 3 | 0 | 0 | — | 0 | 7 | — | 3 | 2 | 0 | — | — | 0 | — | 0 | — | — |
| | 1 | | | | | | | | 2 | 2 | 8 | 3 | 9 | 9 | 9 | 5 | 9 | 9 | 9 | 8 | 7 | 7 |
| 14 | 10 | 0 | 0 | 0 | 0 | 0 | 0 | 0 | 1 | 1 | 1 | 0 | 2 | 2 | 3 | 0 | 1 | 9 | 3 | 1 | 1 | 0 |
| | 1 | | | | | | | | 3 | 2 | 9 | 3 | 8 | 8 | 9 | 0 | 0 | 7 | 0 | 0 | 0 | 0 |
| 15 | 10 | 0 | 0 | 0 | 0 | 0 | 0 | 0 | 0 | 0 | 1 | 0 | 0 | 1 | 0 | — | — | 0 | — | — | — | — |
| | 1 | | | | | | | | 1 | 3 | 8 | 7 | 8 | 9 | 9 | 0 | 0 | 0 | 0 | 0 | 0 | 0 |
| 16 | 10 | 0 | 0 | 0 | 0 | 0 | 0 | 0 | 0 | 0 | 0 | 0 | 2 | 4 | 1 | — | — | — | — | — | — | — |
| | 1 | | | | | | | | 3 | 3 | 8 | 4 | 8 | 8 | 3 | 0 | 0 | 0 | 0 | 0 | 0 | 0 |
| 17 | 10 | 0 | 0 | 0 | 0 | 0 | 1 | 0 | 0 | 0 | 2 | 0 | 0 | 0 | 0 | — | — | — | — | — | — | — |
| | 1 | | | | | | | | 5 | 3 | 8 | 1 | 7 | 9 | 7 | 0 | 0 | 5 | 0 | 0 | 0 | 0 |
| 18 | 10 | 0 | 0 | 0 | 0 | 0 | 0 | 0 | 0 | 1 | 0 | 0 | 3 | 0 | 0 | — | — | 0 | — | — | — | — |
| | 1 | | | | | | | | 1 | 2 | 7 | 2 | 9 | 9 | 9 | 0 | 0 | 0 | 0 | 0 | 0 | 0 |
| 19 | 10 | 6 | 3 | 8 | 0 | 0 | 0 | 0 | 0 | 0 | 0 | 0 | 2 | 1 | 0 | 0 | 0 | 0 | 0 | 0 | 0 | 0 |
| | 1 | | | | | | | | 7 | 3 | 9 | 2 | 8 | 8 | 7 | 2 | 2 | 9 | 0 | 7 | 1 | 0 |
| 21 | 10 | 0 | 0 | 0 | 0 | 0 | 0 | 0 | 0 | 0 | 6 | 0 | 3 | 2 | 0 | 0 | 0 | 9 | 0 | 0 | 0 | 0 |
| | 1 | | | | | | | | 1 | 1 | 7 | 2 | 8 | 7 | 5 | 0 | 0 | 0 | 0 | 0 | 0 | 0 |
| 23 | 10 | 0 | 0 | 0 | 0 | 0 | 0 | 0 | 0 | 0 | 0 | 0 | 1 | 3 | 1 | 0 | 0 | 0 | 0 | 0 | 0 | 0 |
| | 1 | | | | | | | | 1 | 1 | 6 | 2 | 9 | 9 | 5 | 0 | 0 | 0 | 0 | 0 | 0 | 0 |
| 24 | 10 | 0 | 0 | 4 | 0 | 0 | 0 | 0 | 0 | 0 | 0 | 0 | 0 | 1 | 0 | 0 | 0 | 0 | 0 | 5 | 0 | 0 |
| | 1 | | | | | | | | 2 | 2 | 7 | 4 | 8 | 7 | 5 | 0 | 0 | 9 | 0 | 0 | 0 | 0 |
| 25 | 10 | — | — | — | — | — | — | — | 0 | 0 | 0 | 0 | 2 | 3 | 1 | 0 | 0 | 0 | 0 | 0 | 0 | 1 |
| | 1 | | | | | | | | 3 | 3 | 7 | 3 | 8 | 8 | 8 | 4 | 3 | 9 | 0 | 5 | 0 | 1 |
| 26 | 10 | 0 | 0 | 4 | 0 | 0 | 0 | 0 | 0 | 0 | 1 | 0 | 1 | 4 | 0 | 0 | 0 | 7 | 0 | 0 | 0 | 0 |
| | 1 | | | | | | | | 5 | 3 | 8 | 2 | 7 | 4 | 5 | 0 | 0 | 9 | 0 | 0 | 0 | 0 |
| 27 | 10 | 4 | 4 | 6 | 0 | 0 | 0 | 0 | 0 | 0 | 4 | 1 | 5 | 4 | 0 | 0 | 0 | 5 | 0 | 0 | 0 | 0 |
| | 1 | | | | | | | | 4 | 7 | 7 | 2 | 8 | 9 | 7 | 4 | 7 | 9 | 0 | 2 | 2 | 2 |
| | | | | | | | | | 0 | 1 | 0 | 0 | 0 | 1 | 1 | 0 | 2 | 7 | 0 | 0 | 0 | 0 |

We claim as our invention:

1. An oxazoline of the formula $$\begin{array}{c} CH_2\text{---}O \\ R_2\text{---}C\phantom{xx}\diagdown \\ \phantom{R_2\text{---}}C\text{---}R_1 \\ \phantom{R_2\text{---}C}\diagup N \\ CH_2OR_3 \end{array}$$

wherein $R_2$ represents methyl or ethyl, $R_3$ represents benzyl, and $R_1$ represents phenyl, 4-nitrophenyl, benzyl, methyl, 4-methoxphenyl, 4-chlorophenyl, 3-pyridyl, 4-fluorophenyl, 2-furyl, decyl, 4-pyridyl, p-tolyl, styryl, 2-propenyl, o-tolyl, trifluoromethyl, 2-chlorobenzyl or 2-methoxyphenyl, and when $R_1$ represents phenyl $R_3$ then additionally represents 2-chlorobenzyl, 4-chlorobenzyl, 2,6-dichlorobenzyl, 4-methylbenzyl, 3-methylbenzyl or 4-nitrobenzyl.

2. 4-Benzyloxymethyl-2-(2-furyl)-4-methyl-2-oxazoline.

3. 4-Benzyloxymethyl-4-methyl-2-(3-pyridyl)-2-oxazoline.

4. 4-Benzyloxymethyl-4-methyl-2-styryl-2-oxazoline.

5. 4-Benzyloxymethyl-4-methyl-2-phenyl-2-oxazoline.

6. 4-Benzyloxymethyl-4-methyl-2-(4-nitrophenyl)-2-oxazoline.

* * * * *